(12) United States Patent
Brodnick et al.

(10) Patent No.: US 7,305,262 B2
(45) Date of Patent: Dec. 4, 2007

(54) APPARATUS AND METHOD FOR ACQUIRING OXIMETRY AND ELECTROCARDIOGRAM SIGNALS

(75) Inventors: Donald E. Brodnick, Cedarburg, WI (US); Paul S. Schluter, Whitefish Bay, WI (US); James M. Gray, Fox Point, WI (US); George M. Hutchinson, Milwaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 475 days.

(21) Appl. No.: 10/732,985

(22) Filed: Dec. 11, 2003

(65) Prior Publication Data

US 2005/0131282 A1   Jun. 16, 2005

(51) Int. Cl.
*A61B 5/00* (2006.01)
*A61B 5/04* (2006.01)
(52) U.S. Cl. ............... 600/324; 600/509; 600/554
(58) Field of Classification Search ........... 600/323, 600/324, 338, 509, 554
See application file for complete search history.

(56) References Cited

U.S. PATENT DOCUMENTS

| 4,387,723 | A | * | 6/1983 | Atlee, III et al. ........... 600/554 |
|---|---|---|---|---|
| 4,700,708 | A | | 10/1987 | New, Jr. et al. |
| 4,938,218 | A | * | 7/1990 | Goodman et al. ........... 600/338 |
| 5,025,791 | A | * | 6/1991 | Niwa ........................ 600/483 |
| 5,131,401 | A | * | 7/1992 | Westenskow et al. ....... 600/554 |
| 5,623,937 | A | | 4/1997 | Sasaki |
| 5,957,860 | A | | 9/1999 | Rodiera Olive |
| 6,023,541 | A | * | 2/2000 | Merchant et al. ............ 385/20 |
| 6,047,203 | A | * | 4/2000 | Sackner et al. ............ 600/388 |
| 6,643,531 | B1 | | 11/2003 | Katarow |
| 2002/0099277 | A1 | * | 7/2002 | Harry et al. ............... 600/301 |
| 2002/0188205 | A1 | * | 12/2002 | Mills ........................ 600/481 |
| 2003/0109772 | A1 | * | 6/2003 | Mills ........................ 600/310 |

FOREIGN PATENT DOCUMENTS

WO   WO 03 084396   10/2003

OTHER PUBLICATIONS

S/5™ NeuroMuscular Transmission Module, M-NMT, 2000, Datex-Ohmeda.

* cited by examiner

*Primary Examiner*—Eric F Winakur
(74) *Attorney, Agent, or Firm*—Andrus, Sceales, Starke & Sawall, LLP

(57) ABSTRACT

A method and apparatus for acquiring pulse oximetry and electrocardiogram signals from an appendage of a patient. The apparatus can include a substrate that can be attached to the appendage of the patient, an emitter coupled to the substrate, a detector coupled to the substrate, and an electrode coupled to the substrate. The apparatus can generate a blood oxygen saturation output signal based on radiation received by the detector. The apparatus can also generate a reference or non-reference electrocardiogram signal. The apparatus can include a neural-muscular transmission device.

42 Claims, 6 Drawing Sheets

APPARATUS AND METHOD FOR ACQUIRING OXIMETRY AND ELECTROCARDIOGRAM SIGNALS

BACKGROUND OF THE INVENTION

The present invention relates to patient monitoring, and more specifically to acquiring oximetry and electrocardiogram signals.

Conventional oximeter sensors are generally only capable of providing blood oxygen saturation data. However, oximeter sensors are often used at the same time that an electrocardiogram is being acquired. Electrocardiogram instruments require many design considerations, as described in more detail below. Conventionally, these design considerations are addressed with electrodes and an ECG instrument that are independent of the oximeter sensor.

As used herein, the term "ECG" refers to a standard ten-electrode, twelve-lead electrocardiogram or any non-standard electrocardiogram, as are known to one of ordinary skill in the art. The term "ECG signal" or "ECG output signal" refers to one or more leads or channels of data. The term "channel of ECG data" refers to a single lead or a single channel. The term "ECG instrument" refers to any acquisition, analysis, signal generation, and/or monitoring equipment that receives ECG signals from electrodes.

An ECG instrument measures voltage potentials between electrodes or combinations of electrodes attached to a patient. In a minimum configuration, one channel of ECG data is measured between two electrodes. To obtain more channels, additional electrodes are needed. Typically, the voltage between the electrodes (i.e., the differential voltage) is relatively low in amplitude (e.g., approximately one mV). Accordingly, high amplification is needed by the ECG instrument to raise the differential voltage. The body of the patient often has a common mode voltage that is very high in comparison to the differential voltage. It is understood by those of ordinary skill in the art that a high common mode rejection ratio ("CMRR") and a high input impedance are required for an ECG instrument to amplify a low differential voltage in the presence of large common mode voltages in order to acquire an ECG signal of adequate diagnostic quality [i.e., adequate voltage resolution, signal-to-noise ratio ("SNR"), and frequency bandwidth].

For applications in which an ECG signal of reduced quality is adequate (e.g., less than about eight bit resolution for a heart rate monitor in an exercise bicycle, a defibrillator, or an event recorder), the lower frequencies (e.g., less than approximately 0.6 Hz) and the higher frequencies (e.g., greater than approximately 40 Hz) can be filtered from the ECG signal. For these applications, the heart rate monitor may use only two electrodes and a relatively low-cost amplifier.

To avoid the high cost and difficult design of a high CMRR amplifier, an ECG instrument can include a third electrode with a low impedance path between the patient and the ECG instrument. The third electrode is generally referred to as the right leg ("RL") electrode, the common electrode, or the reference electrode. The reference electrode does not serve as a positive input or a negative input to the ECG amplifier(s). Only one reference electrode is necessary, even if many other electrodes are used to acquire several other channels of ECG data. The reference electrode can be positioned on the patient's body in any suitable manner known in the art.

When monitoring infants, especially neonates, the application of many adhesive electrodes to the skin is particularly undesirable. The body surface of an infant is often so small that electrodes can cover relatively large areas of the infant's body. The skin of a neonate is extremely fragile and removing electrodes can easily tear the skin increasing infection risk and pain to the infant. Each electrode also requires a leadwire to connect the electrode to the ECG instrument. Additional electrodes and leadwires decrease the caregiver's ability to access the infant. Additional electrodes also add cost in materials and labor, and increase the time it takes to prepare an infant for monitoring.

Conventional patient monitors often acquire ECG signals, an impedance respiration signal, and a pulse oximeter signal from a patient. The combination of these three monitoring parameters is generally referred to as a cardio-respirogram ("CRG") signal or a pneumogram signal. The CRG signal is of special value in the care of a neonate. To acquire CRG signals, the patient monitor is generally connected to three electrodes for acquiring one channel of ECG data and an impedance respiration signal. A separate transducer, the pulse oximeter sensor, is often attached to an ear lobe, a finger, a toe or another body surface. The pulse oximeter sensor generally illuminates the skin with two colors of light (e.g., red and infra-red) and measures the reflected or transmitted light to determine the level of oxygen saturation of the blood.

BRIEF DESCRIPTION OF THE INVENTION

It is desired by caregivers to attach as few electrodes as possible to patients, especially infants. In one embodiment, the invention provides a method of acquiring pulse oximetry and ECG signals from a patient, including attaching a single transducer to a patient, acquiring a pulse oximetry signal with the single transducer, and acquiring a reference or non-reference ECG signal with the single transducer.

In some embodiments, the invention provides a device for acquiring pulse oximetry and ECG signals from an appendage of a patient. The device can include a substrate that can be attached to the appendage of the patient, at least one emitter coupled to the substrate, at least one detector coupled to the substrate, and an electrode coupled to the substrate. The emitter can be positioned to emit radiation through the appendage, and the electrode can generate a reference or non-reference ECG signal. The detector can be positioned to receive the radiation emitted through the appendage, and can generate a pulse oximetry signal based on the received radiation.

DETAILED DESCRIPTION OF THE INVENTION

Figure 1:
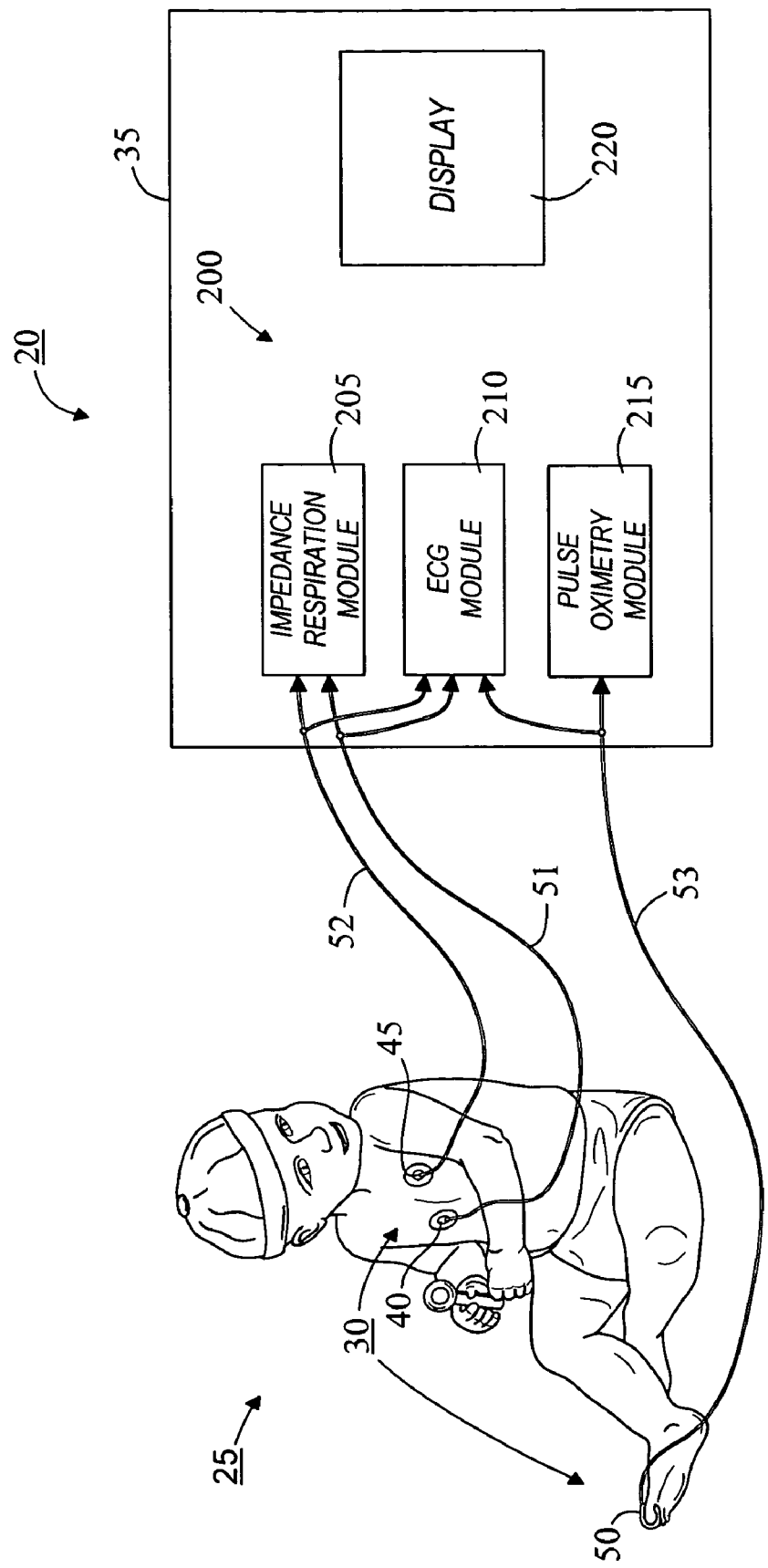
FIG. 1 is a schematic illustration of a monitoring system embodying the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings and can include electrical connections and couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a monitoring system 20 for monitoring a patient 25, such as an infant or neonate or any other patient, according to one embodiment of the invention. The monitoring system 20 can include several electrodes 30 for acquiring signals from the patient 25 and a monitoring instrument 35 for processing, analyzing, and/or displaying the signals acquired from the patient 25. In one embodiment, the monitoring system 20 can analyze, process, and/or display more than one signal from the patient 25, such as, for example, a single-channel of ECG data, multiple channels of ECG data, an impedance respiration signal, an oximeter signal, a pulse oximeter signal, a CRG signal, or any other suitable patient signal. In other embodiments, the monitoring system 20 can analyze, process, and/or display only one signal from the patient 25, such as, for example, a CRG signal. In further embodiments, the monitoring system 20 can analyze, process, and/or display one or more signals from multiple patients (e.g., for monitoring more than one patient at a remote workstation or for monitoring a mother and a fetus).

The electrodes 30 are coupled to the patient 25 to acquire one or more signals. In one embodiment, the electrodes 30 can acquire at least two signals indicative of at least two patient parameters. For example, the electrodes 30 can acquire one or more channels of ECG data, an impedance respiration signal, a signal indicative of a level of oxygen saturation in the patient's blood, etc. In one embodiment, such as the embodiment illustrated in FIG. 1, the electrodes 30 can acquire a single channel of ECG data from the patient 25.

As shown in FIG. 1, the electrodes 30 include a first electrode 40, a second electrode 45, and a third electrode or transducer 50. The first electrode 40 can be attached to the upper-left portion of the patient's chest. The second electrode 45 can be attached to the upper-right portion of the patient's chest. The transducer 50 can be attached to an appendage of the patient 25 (such as, for example, an ear lobe, a finger, a toe, etc.). In other embodiments, the first electrode 40, the second electrode 45, and the transducer 50 can be arranged and attached to other suitable portions of the patient 25 as is known in the art. In one embodiment, one or more of the electrodes 30 (such as, for example, the first electrode 40 and the second electrode 45), can each include a conventional adhesive pad to attach to the skin of the patient 25.

As shown in FIG. 1, the first electrode 40 can be coupled to the monitoring instrument 35 via a first cable or leadwire 51, and the second electrode 45 can be coupled to the monitoring instrument 35 via a second cable or leadwire 52. Also, the transducer 50 can be coupled to the monitoring instrument 35 via a third cable or leadwire 53. In one embodiment, the first cable 51 and the second cable 52 can be single-wire cables, and the third cable 53 can be a multi-wire cable.

Figure 2:
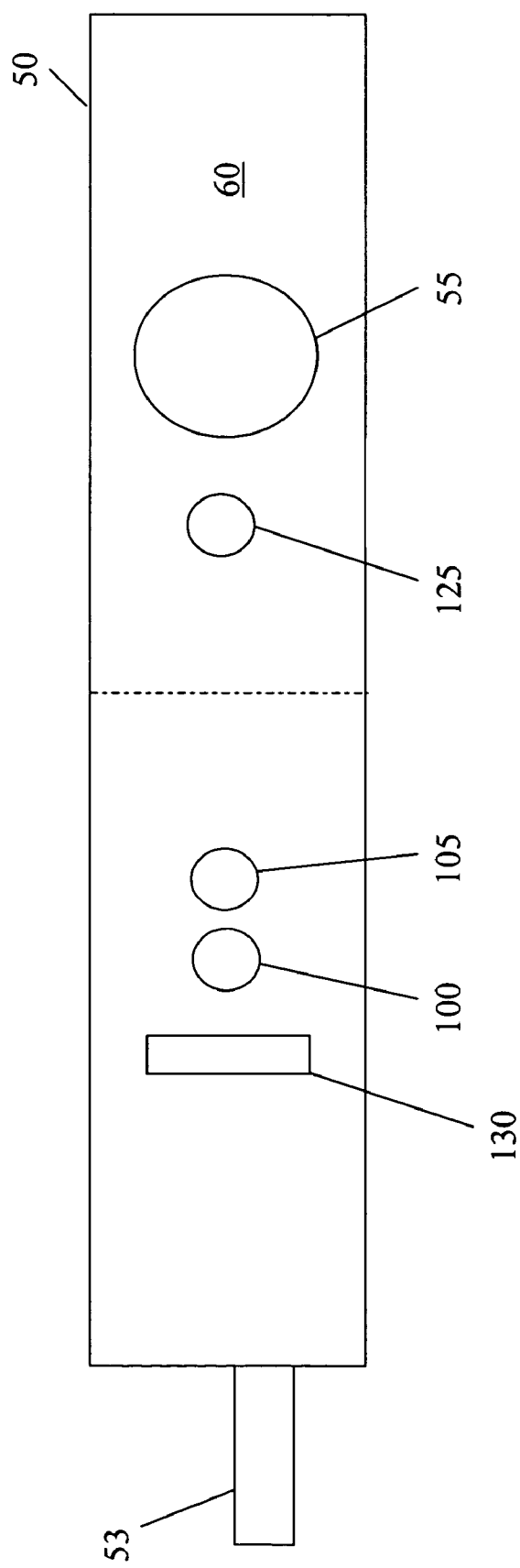
FIG. 2 is a schematic illustration of a transducer for use in the monitoring system of FIG. 1.
Figure 3:
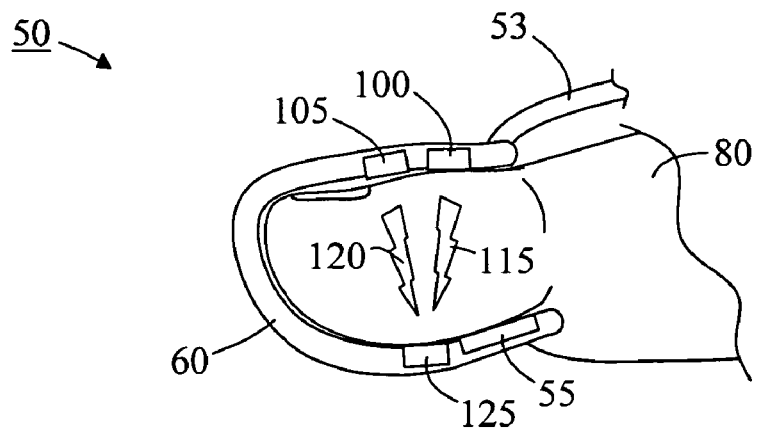
FIG. 3 is a schematic illustration of the transducer of FIG. 2 attached to a patient's appendage.

As shown in FIGS. 2 and 3, the transducer 50 can be a pulse oximeter transducer including an electrode 55 that functions as a reference or non-reference electrode for one or more ECG signals. In simplified instruments that forego the use of a reference electrode, the electrode 55 can act as any suitable terminal of an ECG lead. For example, the electrode 55 can act as a standard right arm electrode when attached to a finger on the patient's right hand. When attached to a toe of the left foot, the electrode 55 can act as a standard left leg or left foot electrode. When attached to a finger of the left hand, the electrode 55 can act as a standard left arm electrode. When attached to a forehead or ear lobe, the electrode 55 can act as a reference or non-reference electrode for the Frank lead system. The Frank lead system is an alternative set of eight electrode sites used to record three channels of XYZ ECG data (i.e., a vectorcardiogram). Thus, the transducer 50 can be used to acquire a signal indicative of a level of oxygen saturation in the patient's blood and a reference or non-reference ECG signal.

As shown in FIG. 2, the transducer 50 can include a substrate 60 that can be attached to the patient 25 or positioned at least partially on the patient 25. In some embodiments, the substrate 60 can be flexible and can include a suitable adhesive. In another embodiment, the substrate 60 can be substantially rigid, such as in a reusable clam-shell design. In one embodiment, when the substrate 60 is attached to the patient 25 as shown in FIG. 3, the transducer 50 can be positioned at least partially on an appendage 80 of the patient 25 (such as, for example, a toe, a finger, an ear lobe, etc.).

As shown in FIGS. 2 and 3, the transducer 50 can include one or more "emitters" embodied by a first light-emitting diode ("LED") 100 and a second LED 105, each coupled to the substrate 60. The first LED 100 and the second LED 105 can each emit a different wavelength of light 115 and 120 (as shown in FIG. 3) through the appendage 80 of the patient 25. In one embodiment, the first LED 100 can emit a red wavelength 115 and the second LED 105 can emit an infra-red wavelength 120. In other embodiments, the transducer 50 can include more or less LEDs than those shown in FIGS. 2 and 3. In other embodiments, the transducer 50 can include LEDs that each emit light having different wavelengths than those described with respect to FIGS. 2 and 3. Rather than LEDs, other suitable light-emitting devices can be used to emit light toward or through the patient 25. Also, any suitable wavelength of light can be emitted toward or through the patient 25. In one embodiment, the transducer 50 can include a photo plethysmograph (PPG) sensor (not shown) having a single LED. The PPG sensor is generally capable of sensing at least heart rate, blood pressure, and perfusion.

The transducer 50 can also include one or more light sensors or detectors 125 positioned to receive the different wavelengths of light 115 and 120 emitted from the first LED 100 and the second LED 105, respectively. As shown in FIG. 3, the detector 125 can be positioned on the substrate 60 to receive wavelengths 115 and 120 that pass through the appendage 80 when the substrate 60 is properly attached to the patient 25.

As noted above, the transducer 50 can include an electrode 55 that serves as an electrode when the monitoring system 20 acquires a single or multiple channels of ECG data. In one embodiment, the electrode 55 can be coupled, electrically and/or physically, to the detector 125, as will be discussed below with respect to FIG. 4. In another embodiment, the electrode 55 can be isolated, electrically and/or physically, from the detector 125 and the additional components of the transducer 50, as will be discussed below with respect to FIG. 5.

Figure 4:
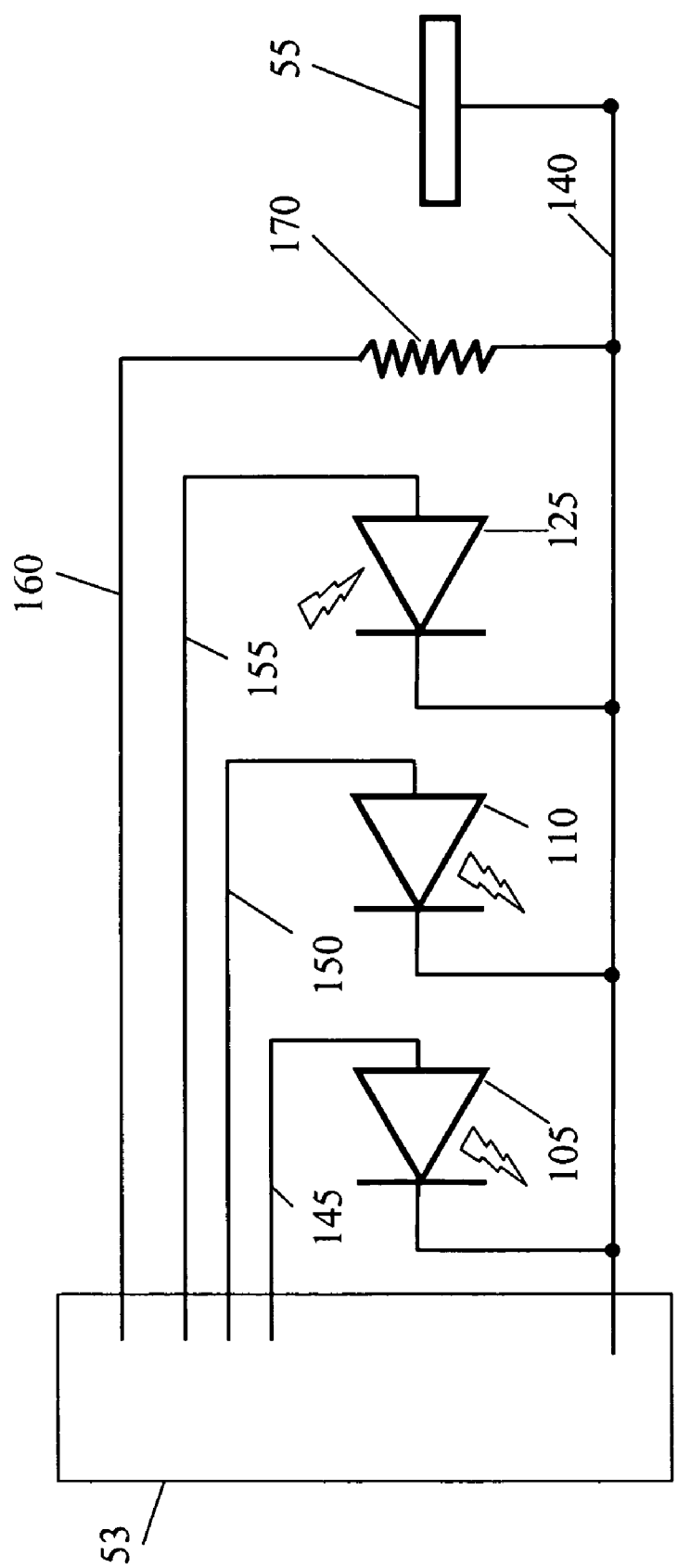
FIG. 4 is an electrical schematic diagram of one embodiment of the transducer of FIG. 2.

In one embodiment, as shown in FIG. 4, the electrode 55 can be electrically coupled to the detector 125 by a reference wire 140. In this embodiment, the cable 53 coupling the transducer 50 to the monitoring instrument 35 can be a five-wire connection cable. The five-wire connection cable 53 can include a first wire 145, a second wire 150, a third wire 155, a fourth wire 160, and the reference wire 140. The first LED 105 can be coupled between the first wire 145 and the reference wire 140. The second LED 110 can be coupled between the second wire 150 and the reference wire 140. The detector 125 can be coupled between the third wire 155 and the reference wire 140. A resistor 170 can be coupled between the fourth wire 160 and the reference wire 140.

Figure 5:
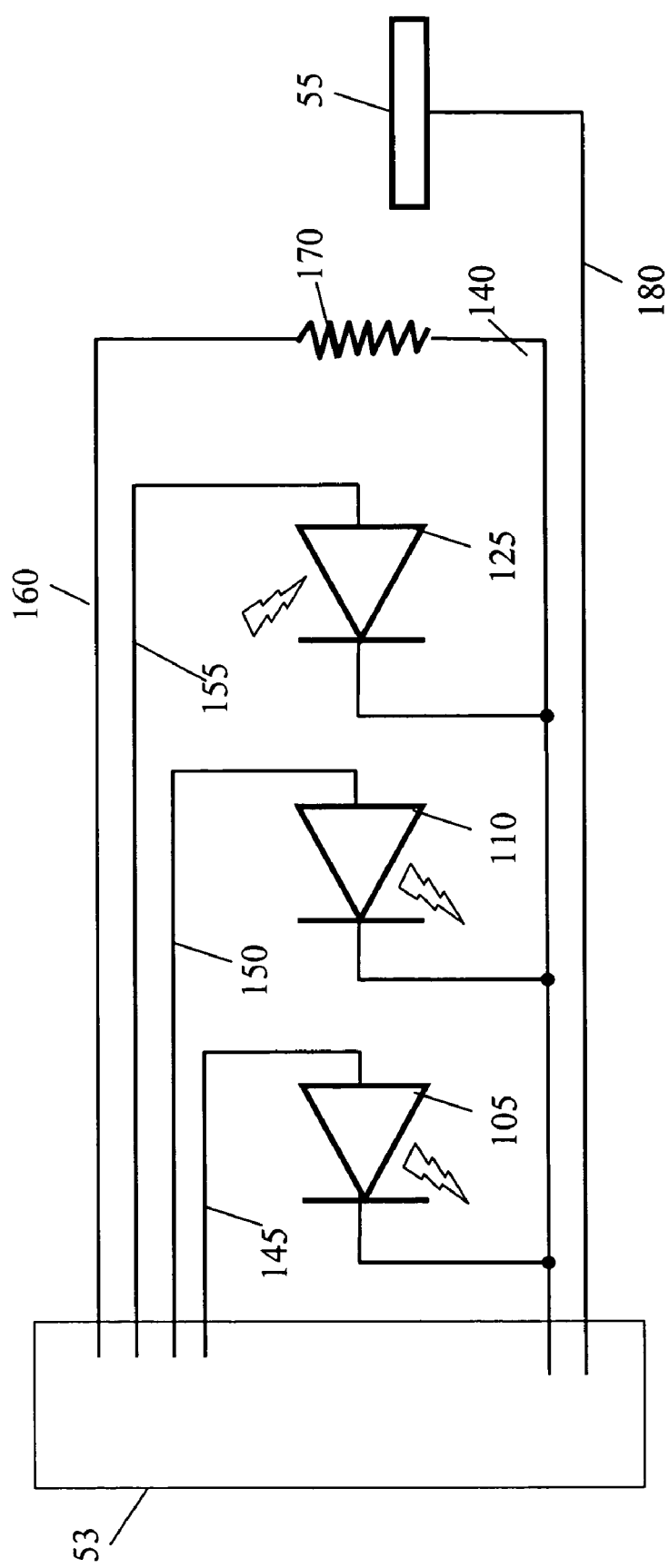
FIG. 5 is an electrical schematic diagram of another embodiment of the transducer of FIG. 2.

In another embodiment, as shown in FIG. 5, the electrode 55 of the transducer 50 can be electrically isolated from the detector 125 by being coupled to an isolated reference wire 180. In one embodiment, the cable 53 coupling the transducer 50 to the monitoring instrument 35 can be a single connection cable including as many wires as necessary. The reference wire 140 can be a reference wire for the oximetry components, while the reference wire 180 can be a reference wire for the reference electrode 55 and the ECG signals.

As shown in FIG. 1, the monitoring instrument 35 can include one or more modules 200 for processing the signals acquired from the electrodes 30. For example, the modules 200 can include an impedance respiration module 205 for determining the impedance respiration of the patient 25. The modules 200 also can include an ECG module 210 for generating and analyzing a single or multiple channels of ECG data. In other embodiments, the ECG module can include more than one single-channel module (e.g., for monitoring more than one patient at a remote workstation or for monitoring a mother and a fetus). The modules 200 can further include a pulse oximetry module 215 for determining a level of oxygen saturation in the patient's blood. The monitoring instrument 35 can also include modules in addition to those shown and described with respect to FIG. 1. However, the monitoring instrument 35 can include fewer modules than shown and described with respect to FIG. 1.

The monitoring instrument 35 can also include a display 220. The display 220 can display one or more signals to a user or caregiver. The display 220 can display patient parameter signals such as one or more ECG signals, an impedance respiration signal, an cardio-respirogram, etc. In some embodiments, the display 220 can include a monitor for electronically displaying a signal. The display 220 in some embodiments can include a printer or an electrocardiograph for displaying a signal.

Figure 6:
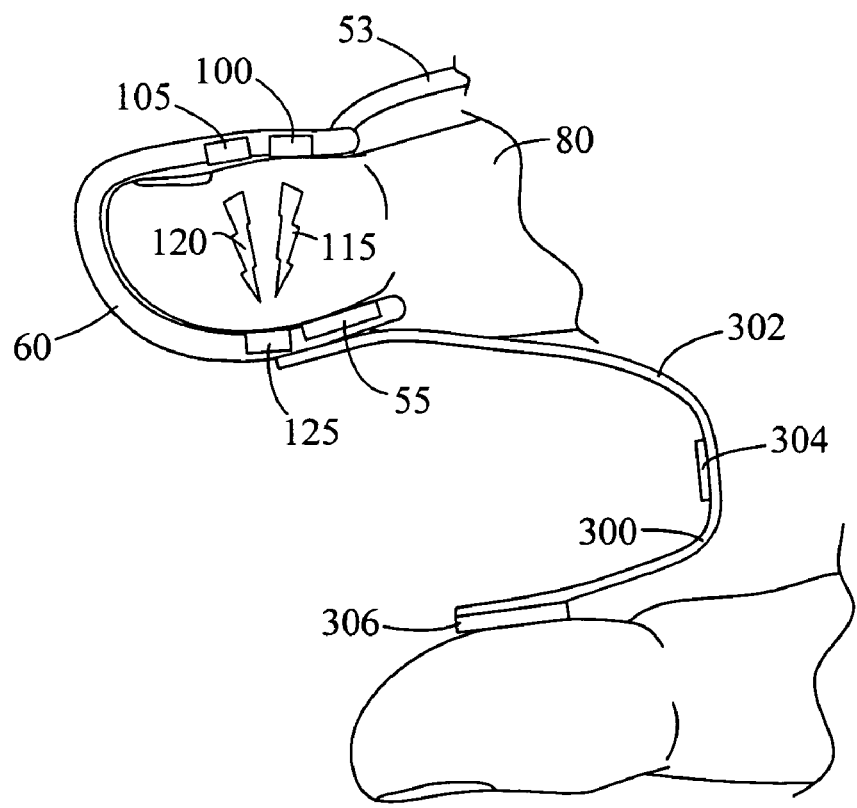
FIG. 6 is a schematic illustration of a transducer attached to a patient's appendage according to another embodiment of the invention.

FIG. 6 illustrates an alternative embodiment of the transducer 50. In addition to the components of the transducer 50 shown in FIGS. 2 and 3, the alternative embodiment of the transducer 50 can include a neural-muscular transmission (NMT) device 300. The NMT device 300 can include a support member 302 (e.g., a semi-rigid support member) and either a flexure sensor 304 or a pressure sensor 306. The NMT device 300 can be connected to an NMT circuit (not shown) that can apply a stimulus to a peripheral motor nerve, such as the ulnar nerve at the patient's wrist or elbow. Due to the stimulus, the patient's adductor pollicis muscle can contract causing the patient's thumb to twitch inward toward the patient's fingers. The NMT device 300 can measure the strength of this muscle contraction between the support member 302 and the flexure sensor 304 (which can be located at a point of maximum bending on the support member 302). Alternatively, the NMT device 300 can measure the strength of the muscle contraction between the support member 302 and the pressure sensor 306 (which can be located on the patient's thumb). In some embodiments, the support member 302 can be fitted into the space between the patient's index or middle finger and the patient's thumb. In some embodiments, the support member 302 can include a channel (not shown) along its length to partially enclose the patient's finger and thumb.

In some embodiments (unlike the embodiment shown in FIG. 6), the support member 302 does not extend over the electrode 55. In some embodiments, the flexure sensor 304 and/or the pressure sensor 306 can include a piezo-electric film or a stain gauge to perform the flexure or pressure sensing, respectively. In some embodiments, sensor 306 may be a motion sensor such as an accelerometer. One suitable NMT sensor is the S/5™ NeuroMuscular Transmission Module M-NMT manufactured by Datex-Ohmeda, Inc. (e.g., Part Number 888418 or 897439).

NMT is a measurement technology for monitoring the depth of muscle block, which is an important aspect of anesthesia. Although measuring $SpO_2$ by oximetry at a finger is made more difficult because of finger or hand motion, thumb motion is what is generated during anesthesia monitoring with NMT. Also, both oximetry and NMT measurement techniques are valuable at the same time in patients undergoing surgery or intubation. Although the $SpO_2$ measurement is not made at the thumb, thumb motion is likely to cause vibrations in the entire hand. As a result, the SpO2 measurement is conventionally performed on a patient's right hand and the NMT measurement is conventionally performed on the patient's left hand. However, two separate measurements requires additional equipment and cable access to both sides of the patient, in addition to complicating the delivery of care. Also, if NMT and $SpO_2$ are measured with separate and independent devices, the NMT device often interferes electrically with the $SpO_2$ device.

In light of these problems, in one embodiment of the invention, the NMT device 300 and the transducer 50 can be connected to the monitoring system 20 by a single cable 53 in order to operate the NMT device 300 and the transducer 50 in a harmonious, non-interfering manner. Also, the NMT device 300 and the transducer 50 being connected to the monitoring system 20 by a single cable 53 further reduces the number of cables connected to the patient. By operating both devices from the same monitoring system 20, the SpO$_2$ measurements can be disabled when the NMT device 300 is operating. The NMT device 300 may operate for about 2 to 5 seconds, but may only operate a few times each minute. Combining the NMT device 300 and the transducer 50 into a single unit also allows measurements to be taken on only one hand of the patient. Therefore, adaptive filtering techniques may be used, triggered or correlated to the activation of the NMT stimulation circuit or the response of the NMT sensor, to attenuate the consequent artifacts in the ECG signals and/or the SpO$_2$ signals.

Figure 7:
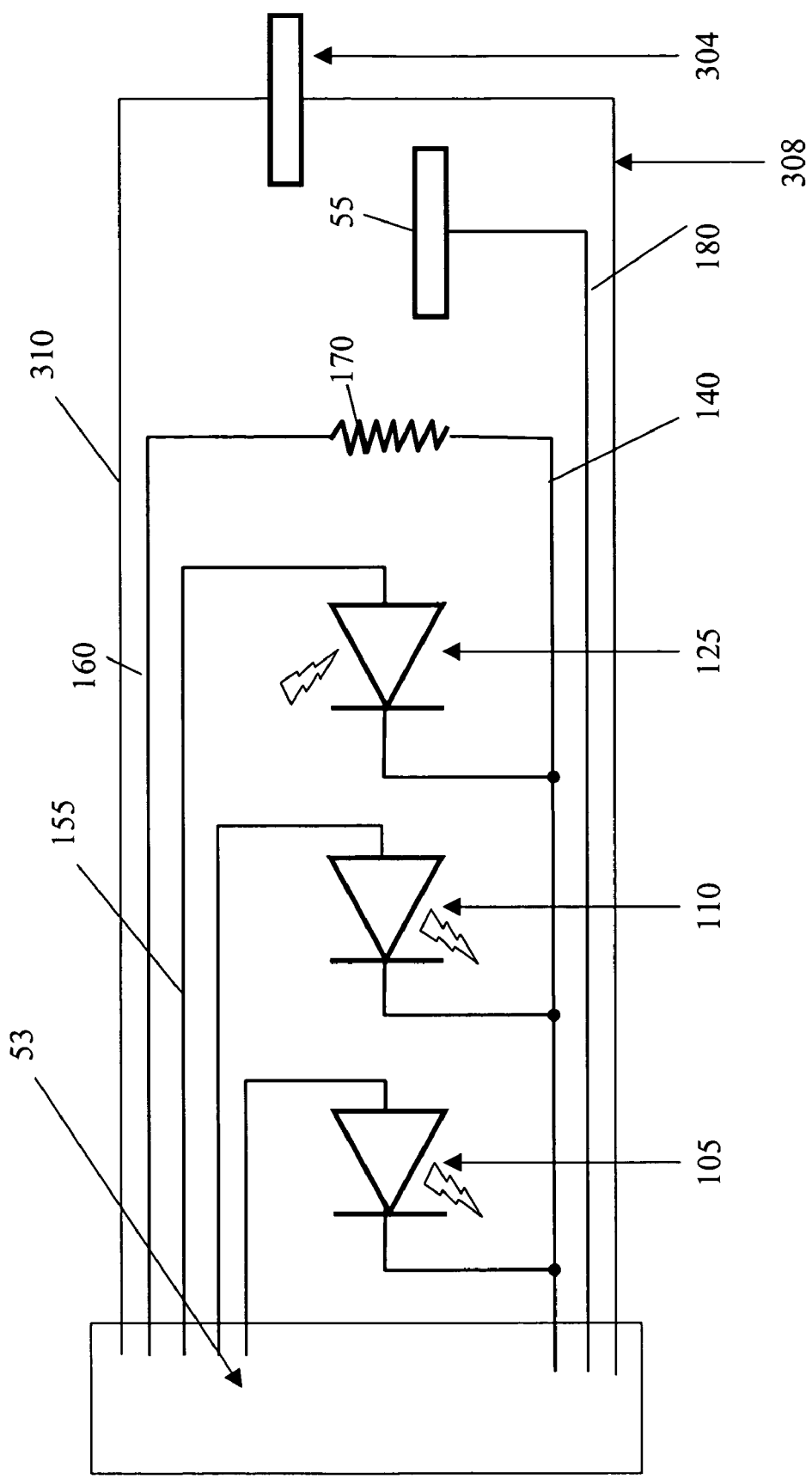
FIG. 7 is an electrical schematic diagram of one embodiment of the transducer of FIG. 6.

In the alternative embodiment of the transducer 50, as shown and described with respect to FIGS. 6 and 7, the reference wire 140 can be a reference wire for the oximetry components, the reference wire 180 can be a reference wire for the electrode 55 and the ECG signals, and an additional reference wire 308 (as shown in FIG. 7) can be a reference wire for the flexure sensor 304 of the NMT device 300. However, in some embodiments, the NMT reference wire 308 can be combined with one or both of the reference wires 140 and 180. The flexure sensor 304 can include a piezo-electric film that produces a voltage between the NMT reference wire 308 and an NMT sensing wire 310.

In one embodiment of the method of the invention, a caregiver can attach the first electrode 40, the second electrode 45, and the transducer 50 to the patient 25 (such as, for example, an infant or neonate) in order to obtain an ECG signal and a signal indicative of a level of oxygen saturation. In another embodiment of the method of the invention, a caregiver can attach the transducer 50 to a finger of the patient 25 and the NMT device 300 to the thumb of patient 25. Thus, the monitoring system 20 can provide a reduction (with respect to conventional systems) in the total number of connections and lead wires attached to the patient 25. It should be understood that although the appended claims refer to acts of the method of the invention in a particular order, the scope of the appended claims is not to be limited to any particular order. The acts specified in the appended claims can be performed in various different orders and still fall within the scope of the invention.

Various features and advantages of the invention are set forth in the following claims.

The invention claimed is:

1. A method of acquiring pulse oximetry and electrocardiogram signals from a patient, the method comprising:
configuring a single transducer and attaching the single transducer to a finger of a patient, wherein the single transducer includes a single electrode such that when the single transducer is attached to the finger of the patient, the single transducer is configured to acquire a pulse oximetry signal and acquire an electrocardiogram signal with the single electrode, wherein the acquired electrocardiogram signal is either one of a reference electrocardiogram signal or a non-reference electrocardiogram signal, and further wherein a neural-muscular transmission device is coupled to the single transducer, and includes a support member that extends to a thumb of the patient;
acquiring the pulse oximetry signal and the electrocardiogram signal with the single electrode;
stimulating the patient with the neural-muscular transmission device; and
measuring the strength of muscle contraction caused by the stimulating step;
wherein the acquired pulse oximetry signal is processed to account for effects of the stimulating step to provide an artifact free pulse oximetry signal.

2. The method of claim 1 and further comprising generating a blood oxygen saturation output signal based on the pulse oximetry signal.

3. The method of claim 1 and further comprising attaching at least one additional electrode to the patient, and acquiring at least one additional electrocardiogram signal from the patient, wherein the at least one additional electrocardiogram signal is the reference electrocardiogram signal if the single transducer acquires the non-reference electrocardiogram signal, and further wherein the at least one additional electrocardiogram signal is the non-reference electrocardiogram signal if the single transducer acquires the reference electrocardiogram signal.

4. The method of claim 3 and further comprising generating at least one electrocardiogram output signal based on the reference electrocardiogram signal and the at least one non-reference electrocardiogram signal.

5. The method of claim 4 and further comprising acquiring an impedance respiration signal from the patient.

6. The method of claim 5 and further comprising generating a cardio-respirogram output signal based on the pulse oximetry signal, the reference electrocardiogram signal, the at least one non-reference electrocardiogram signal, and the impedance respiration signal.

7. The method of claim 3 and further comprising generating at least one channel of electrocardiogram output data based on the reference electrocardiogram signal and the at least one non-reference electrocardiogram signal.

8. The method of claim 1 and further comprising attaching the single transducer and at least two additional electrodes to the patient, and acquiring signals to generate a cardio-respirogram output signal.

9. The method of claim 1 and further comprising filtering at least one of the pulse oximetry signal and the electrocardiogram signal acquired when the neural-muscular transmission signal was being acquired.

10. The method of claim 1 and further comprising ignoring at least one of the pulse oximetry signal and the electrocardiogram signal acquired when the neural-muscular transmission signal was being acquired.

11. The method of claim 1 and further comprising using the neural-muscular transmission signal to monitor anesthesia.

12. The method of claim 1 wherein the single transducer includes an oximeter having at least two light-emitting diodes.

13. The method of claim 1 wherein the single transducer includes a photo plethysmograph sensor having at least one light-emitting diode.

14. A device for acquiring pulse oximetry and electrocardiogram signals from an appendage of a patient, the device comprising:
a substrate that can be attached to the appendage of the patient;
at least one emitter coupled to the substrate, the at least one emitter positioned to emit radiation through the appendage;
at least one detector coupled to the substrate, the at least one detector positioned to receive the radiation emitted through the appendage, the at least one detector generating a pulse oximetry signal based on the received radiation;

an electrode coupled to the substrate, the electrode configured to generate either one of a reference electrocardiogram signal or a, non-reference electro-cardiogram signal; and a neural-muscular transmission device (NMT), wherein the NMT includes a semi-rigid support member coupled to the substrate and extending in a clam shell shape, such that the NMT measures the strength of muscle contractions of the patient caused by an applied stimulus and said device is configured to provide an artifact free pulse oximetry signal.

15. The device of claim 14 wherein the at least one emitter includes a first red light-emitting diode and a second infra-red light-emitting diode.

16. The device of claim 15 wherein the at least one detector includes a single detector to receive radiation emitted by the first red light-emitting diode and the second infra-red light-emitting diode.

17. The device of claim 14 and further comprising a common reference wire coupled to the electrode and the at least one detector.

18. The device of claim 14 and further comprising an electrocardiogram reference wire coupled to the electrode and an oximetry reference wire coupled to the at least one detector in order to isolate the electrode from the at least one detector.

19. The device of claim 14 and further comprising a multi-wire connector coupled to the at least one emitter, the at least one detector, and the electrode.

20. The device of claim 14 wherein the substrate is sized for attachment to an appendage of at least one of an infant and a neonate.

21. The device of claim 14 wherein the substrate includes an elongated portion adapted to be folded in half over the appendage in order to position the at least one emitter to emit radiation through a first side of the appendage and the at least one detector to receive the emitted radiation through a second side of the appendage.

22. The device of claim 14 and further comprising a processor that filters at least one of the pulse oximetry signal and the electrocardiogram signal acquired when the neural-muscular transmission signal was being acquired.

23. The device of claim 14 and further comprising a processor that ignores at least one of the pulse oximetry signal and the electrocardiogram signal acquired when the neural-muscular transmission signal was being acquired.

24. A system for monitoring pulse oximetry and electrocardiogram signals acquired from a patient, the system comprising:

a transducer including
  a substrate that can be attached to an appendage of the patient,
  at least one emitter coupled to the substrate, the at least one emitter positioned to emit radiation through the appendage,
  at least one detector coupled to the substrate, the at least one detector positioned to receive the radiation emitted through the appendage, the at least one detector generating a pulse oximetry signal, and
  a first electrode coupled to the substrate, the first electrode generating either one of a reference or a non-reference electrocardiogram signal;

at least one second electrode that can be attached to the patient, the at least one second electrode generating a non-reference electrocardiogram signal when the first electrode generates a reference electrocardiogram signal, and generating a reference electrocardiogram signal when the first electrode generates a non-reference electrocardiogram signal; and a monitoring instrument that receives the pulse oximetry signal, the reference electrocardiogram signal, and the non-reference electrocardiogram signal, the monitoring instrument generating a blood oxygen saturation output signal and at least one electrocardiogram output signal; and a neural-muscular transmission device (NMT), wherein the NMT includes a semi-rigid support member coupled to the substrate and extending in a clam shell shape, such that the NMT measures the strength of muscle contractions of the patient caused by an applied stimulus and the monitoring instrument is configured to provide an artifact free pulse oximetry signal.

25. The system of claim 24 wherein the monitoring instrument generates an impedance respiration signal from at least one of the first electrode and the at least one second electrode.

26. The system of claim 25 wherein the monitoring instrument generates a cardiorespirogram output signal based on the pulse oximetry signal, the reference electrocardiogram signal, the at least one non-reference electrocardiogram signal, and the impedance respiration signal.

27. The system of claim 24 wherein the monitoring instrument generates at least one channel of electrocardiogram output data based on the reference electrocardiogram signal and the at least one non-reference electrocardiogram signal.

28. The system of claim 24 wherein the at least one emitter includes a first red light-emitting diode and a second infra-red light-emitting diode.

29. The system of claim 28 wherein the at least one detector includes a single detector to receive radiation emitted by the first red light-emitting diode and the second infra-red light-emitting diode.

30. The system of claim 24 wherein the transducer includes a common reference wire coupled to the first electrode and the at least one detector.

31. The system of claim 24 wherein the transducer includes an electrocardiogram reference wire coupled to the first electrode and an oximetry reference wire coupled to the at least one detector in order to isolate the first electrode from the at least one detector.

32. The system of claim 31 wherein the transducer includes a multi-wire connector coupled to the at least one emitter, the at least one detector, and the first electrode.

33. The system of claim 24 wherein the substrate is sized for attachment to an appendage of at least one of an infant and a neonate.

34. The system of claim 24 wherein the substrate includes an elongated portion adapted to be folded in half over the appendage in order to position the at least one emitter to emit radiation through a first side of the appendage and the at least one detector to receive the emitted radiation through a second side of the appendage.

35. The system of claim 24 wherein the monitoring instrument generates a neural-muscular transmission output signal for monitoring anesthesia.

36. The device of claim 35 wherein the monitoring instrument filters at least one of the pulse oximetry signal and the electrocardiogram signal acquired when the neural-muscular transmission signal was being acquired.

37. The device of claim 35 wherein the monitoring instrument ignores at least one of the pulse oximetry signal and the electrocardiogram signal acquired when the neural-muscular transmission signal was being acquired.

38. A method of acquiring pulse oximetry and electrocardiogram signals from a patient, the method comprising:
- configuring a transducer to include at least one emitter, at least one detector, and a first electrode and attaching the transducer to an appendage of the patient;
- attaching at least one second electrode to the patient wherein the transducer is configured such that a pulse oximetry signal is acquired from the at least one detector and a reference or non-reference electrocardiogram signal is acquired from the first electrode, further wherein the at least one second electrode is configured to acquire a non-reference electrocardiogram signal from the at least one second electrode when the first electrode acquires a reference electrocardiogram signal and a reference electrocardiogram signal when the first electrode acquires a non-reference signal, and further wherein a neural-muscular transmission device is coupled to the transducer, and includes a support member that extends to a thumb of the patient;
- stimulating the patient with the neural-muscular transmission device; and
- measuring the strength of muscle contraction caused by the stimulating step;
- generating a blood oxygen saturation output signal based on the pulse oximetry signal including generating an artifact free pulse oximetry signal during use of the neural-muscular transmission device; and
- generating at least one electrocardiogram output signal based on the reference electrocardiogram signal and the non-reference electrocardiogram signal.

39. The method of claim 38 and further comprising generating an impedance respiration signal based on the first electrode and the at least one second electrode.

40. The method of claim 39 and further comprising generating a cardio-respirogram output signal based on the pulse oximetry signal, the reference electrocardiogram signal, the at least one non-reference electrocardiogram signal, and the impedance respiration signal.

41. The method of claim 38 and further comprising generating at least one channel of electrocardiogram output data based on the reference electrocardiogram signal and the at least one non-reference electrocardiogram signal.

42. A method of acquiring pulse oximetry and electrocardiogram signals from an infant, the method comprising:
- configuring a transducer to include at least one emitter; at least one detector, and a first electrode, and attaching the transducer to a finger of the infant;
- attaching at least two additional electrodes to the infant wherein the transducer is configured such that a pulse oximetry signal is acquired from the detector, a reference electrocardiogram signal is acquired from any one of the electrodes, and at least two non-reference electrocardiogram signals are acquired from the remaining electrodes, and further wherein a neural-muscular transmission device is coupled to the transducer, and includes a support member that extends to a thumb of the patient;
- stimulating the patient with the neural-muscular transmission device; and
- measuring the strength of muscle contraction caused by the stimulating step; and
- generating a blood oxygen saturation output signal based on the pulse oximetry signal including generating an artifact free pulse oximetry signal during use of the neural-muscular transmission device and generating at least one electrocardiogram signal based on the reference electrocardiogram signal and the at least two non-reference electrocardiogram signals.

* * * * *